United States Patent [19]
Esanu

[11] 4,176,193
[45] Nov. 27, 1979

[54] THERAPEUTIC ISOBUTYRAMIDES

[75] Inventor: Andre Esanu, Paris, France

[73] Assignee: Societe d'Etudes de Produits Chimiques, Paris, France

[21] Appl. No.: 962,129

[22] Filed: Nov. 17, 1978

Related U.S. Application Data

[63] Continuation of Ser. No. 778,729, Mar. 17, 1977, abandoned.

[51] Int. Cl.² .................. A01N 9/20; C07C 121/78
[52] U.S. Cl. .............................. 424/304; 260/465 D
[58] Field of Search ................... 260/465 D; 424/304

[56] References Cited

U.S. PATENT DOCUMENTS

| | | | |
|---|---|---|---|
| 2,927,126 | 3/1960 | Pursglove | 260/465 D |
| 3,439,018 | 4/1969 | Brookes et al. | 260/465 D X |
| 3,932,168 | 1/1976 | Stein et al. | 260/465 D X |
| 4,001,427 | 1/1977 | Baker et al. | 424/304 |
| 4,052,432 | 10/1977 | Baker et al. | 260/465 D |

Primary Examiner—Dolph H. Torrence
Attorney, Agent, or Firm—Eyre, Mann, Lucas & Just

[57] ABSTRACT

A method of treating hyperlipemia, hypertriglyceridemia and hyperchoesterodemia is disclosed. The treatment comprises the administration in a pharmaceutically acceptable carrier of an effective amount of a p-halo-N-cyanoalkyl isobutyramide.

1 Claim, No Drawings

THERAPEUTIC ISOBUTYRAMIDES

This is a continuation of application Ser. No. 778,729, filed Mar. 17, 1977 and now abandoned.

This invention relates to new isobutyramides, to a method for their preparation and to therapeutic compositions containing the sames.

The novel isobutyramides of this invention have the following general formula

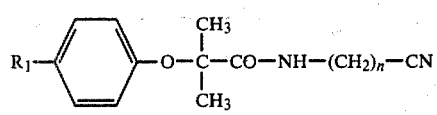

wherein $R_1$ represents a halogen atom and n is an integer from 2 to 6. The new compounds may be prepared according to this invention by the action in stoechiometric proportions of the corresponding acid chloride of the formula:

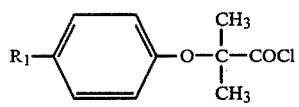

on the appropriate aminoalkyl nitrile derivative of the formula $NH_2-(CH_2)_n-CN$ ($R_1$ and n are ase above defined) in a mixture of polar and non polar solvents.

The new compounds and their acid addition salts are of interest in the therapeutic field and show a hypolipemic, hypotriglyceridemic and hypocholesterolemic activity.

This invention is illustrated by the following examples.

EXAMPLE 1

N-cyanoethyl p-chlorophenoxy isobutyramide

In a 2.5 liter reactor fitted with cooling and stirring means there were poured 1 liter of dry dichloroethane, 74 g of triethylamine and 52 g (0.74 mol) of 3-amino propionitrile. The mixture was stirred and there was then slowly added over a period of period 30 minutes, a solution of 172 g (0.74 mol) of p-chlorophenoxy-isobutyryl chloride in 0.5 liters of dry dichloroethane.

The temperature was maintained below 10° C. during the addition period and then the mixture was refluxed for 4 hours and evaporated to dryness. The product obtained was washed with a sodium carbonate solution, treated with water, extracted with chloroform, dried, treated with diethyl ether and crystallized from di-isopropyl ether.

There was thus obtained 128 g (yield 65%) of a white crystalline product melting at 70° C., the composition of which is in complete agreement with the formula $C_{13}H_{15}N_2O_2Cl$ (molecular weight 266.7).

This compound is insoluble in water but soluble in many organic solvents. The p-chlorophenoxy isobutyric acid chloride was obtained from p-chlorophenoxy isobutyric acid treated by $SOCl_2$ in anhydrous benzene.

EXAMPLE 2

N-cyanoethyl p-fluorophenoxy isobutyramide

The procedure of example 1 was repeated except that the p-chlorophenoxy-isobutyryl chloride was replaced by p-fluorophenoxy-isobutyryl chloride. There was thus obtained, with a yield of 71%, a white crystalline product melting at 75° C. The composition of the product was in agreement with the formula: $C_{15}H_{15}N_2O_2F$; molecular weight 250.2.

EXAMPLE 3

N-cyanobutyl p-chlorophenoxy isobutyramide

The procedure of example 1 was repeated except that 3-amino propionitrile was replaced by 5-amino pentanonitrile; yield 81% of a white crystalline product melting at 88° C. the analysis of which shows a good correspondence with the formula $C_{15}H_{19}N_2O_2Cl$.

The compounds obtained according to this invention have been submitted to toxicological, pharmacological and clinical studies which are summarized thereafter.

TOXICITY

The acute toxicity has been determined per os on mice and rats, by the usual technics. The LD 50 values are respectively 1 g/kg for mice and over 2.4 g/kg for rats for the compound of example 1.

For the compounds of examples 2 and 3, the LD 50 was 1.2 g/kg for both, on mice and over 2.5 g/kg for both, on rats.

The subacute toxicity of the compound of example 1 was researched on rats at the does of 40, 80 and 160 mg/kg (per os) and no difference was noticed between treated and control animals.

PHARMACOLOGY

Triton test.

An experimental hyperlipemia and hyperchlolesterolemia are induced in male rats by an intraperitoneal injection of triton (dose: 5 ml/kg); these rats are treated immediately per os, either by the product of example 1 or by 2-(4-chlorophenoxy)-2methylpropanic acid ethyl ester or by nicotinic acid (three batches of each 10 animals) at the same doses. The best hypocholesterolemic activities are found for the compound of the invention and the first reference compound whereas the best hypotriglyceridemic activities are found for the second reference compound and the compound of invention.

CLINIC 20 patients were treated comparatively, successively by 2-(4-chlorophenoxy) 2-methyl propanoic acid ethyl ester—reference compound—(30 days, 2 g/day) and, after 15 days without treatment, by the compound of example 1—invention compound—(30 days, 2 g/day); the average figures in g/l for initial values, final values and decrease for triglycerids, total cholesterol and total lipids are listed in the following table.

|  | REFERENCE COMPOUND | INVENTION COMPOUND |
|---|---|---|
| Triglycerids |  |  |
| Initial | 1.611 (± 0.098) | 1.59 (± 0.155) |
| Final | 1.137 (± 0.085) | 1.082 (± 0.101) |
| Decrease | 0.474 (± 0.102) | 0.507 (± 0.088) |
| Total cholesterol |  |  |
| Initial | 3.31 (± 0.121) | 3.17 (± 0.151) |
| Final | 2.85 (± 0.170) | 2.70 (± 0.169) |
| Decrease | 0.46 (± 0.107) | 0.47 (± 0.058) |
| Total lipids |  |  |
| Initial | 9.985 (± 0.342) | 9.94 (± 0.454) |
| Final | 8.775 (± 0.491) | 8.367 (± 0.431) |
| Decrease | 1.210 (± 0.244) | 1.572 (± 0.198) |

The activity of the compound of the invention appears similar on the total cholesterol rate but more favourable on the triglycerids and total lipids rates.

PRESENTATION—POSOLOGY

The compound of the invention may be presented in any suitable form for use in human therapy. For instance, a form for oral administration may be a gelatin capsule containing:

| | |
|---|---|
| - compound of any of the examples | 0.500 g |
| - silicic acid | 0.018 g |
| - talc | 0.042 g |
| | 0.560 g |

As to the posology, according to the patients, it may be comprised between 0.5 and 4 g per day.

I claim:

1. A method of treating hyperlipemia, hypertriglyceridemia and hypercholesterodemia comprising the administration in a pharmaceutically acceptable carrier of an effective amount of a compound having the formula:

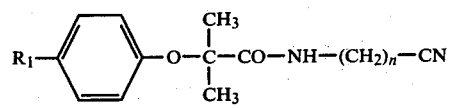

wherein:
$R_1$ is a halogen
$n$ is an integer from 2 to 6.